United States Patent [19]

Lipsey

[11] 4,192,000

[45] Mar. 4, 1980

[54] ELECTRONIC CALORIE COUNTER

[75] Inventor: Elmer M. Lipsey, McLean, Va.

[73] Assignee: Calorie Counter Limited Partnership, Springfield, Va.

[21] Appl. No.: 815,854

[22] Filed: Jul. 14, 1977

[51] Int. Cl.² .............................................. G01L 3/00
[52] U.S. Cl. .................................. 364/415; 250/215; 272/93; 364/410
[58] Field of Search ............... 364/410, 413, 415, 561; 272/70, 93, 100, 114; 73/379–381, 517 R; 235/105, 92 MT, 92 T; 128/2 R; 310/15, 27; 250/215

[56] References Cited

U.S. PATENT DOCUMENTS

| | | | |
|---|---|---|---|
| 3,984,666 | 10/1976 | Barron | 235/92 MT |
| 4,053,755 | 10/1977 | Sherrill | 364/561 |
| 4,100,401 | 7/1978 | Tutt et al. | 235/92 T |
| 4,101,071 | 7/1978 | Brejnik et al. | 235/92 MT |
| 4,144,568 | 3/1979 | Hiller et al. | 364/410 |

*Primary Examiner*—Errol A. Krass
*Attorney, Agent, or Firm*—Schuyler, Birch, McKie & Beckett

[57] ABSTRACT

An electronic calorie counter is disclosed which provides a digital readout of the rate of caloric consumption with exercise by the user by sensing the vertical component of the motion of the user, and translating that motion into electronic impulses. The vertical component of the user's motion is constantly detected using a magneto-electric transducer in combination with means for defining an opto-electric axis in the transducer. The output of the opto-electric means is combined with a clock-controlled gate to provide a burst of impulses over a unit of time which is proportional to the vertical acceleration sensed. The gate output is supplied to a program-controlled processor utilizing a mathematical equation derived to analyze caloric consumption in humans with exercise. The processor is also responsive to several input switches indicating the physical parameters of the individual user in calculating caloric consumption. The microprocessor output, as displayed, comprises the calories consumed by the user over a fixed period of time.

5 Claims, 3 Drawing Figures

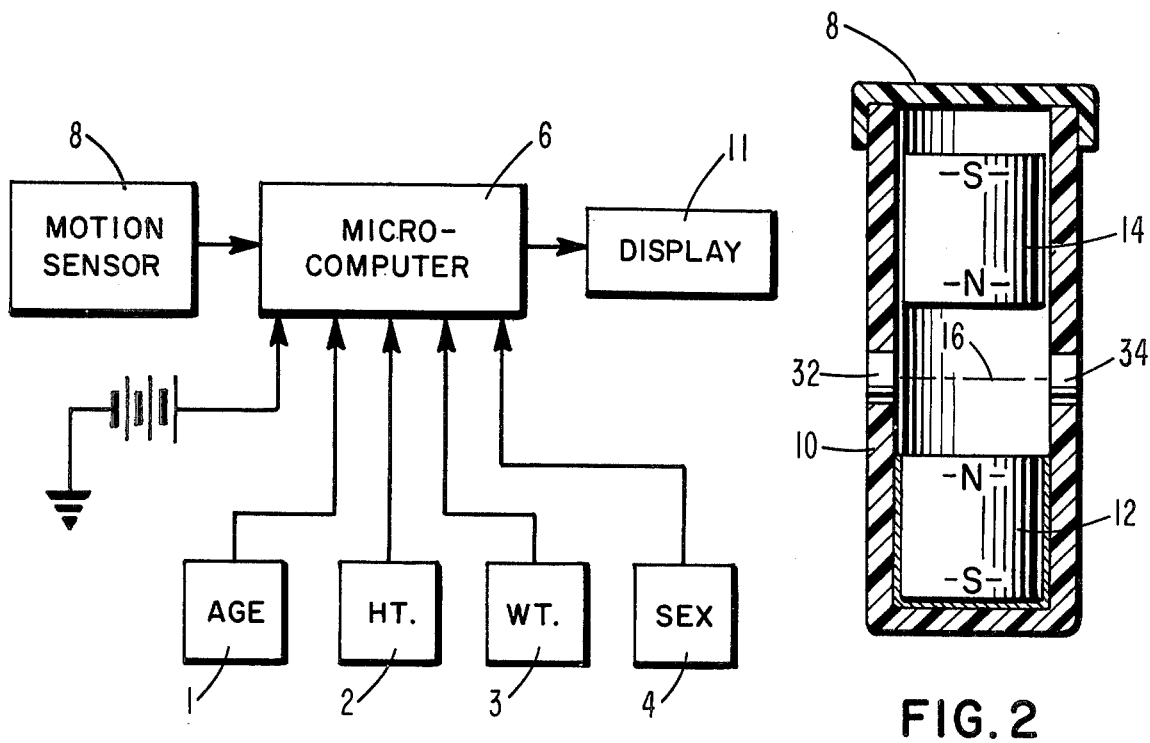
FIG. 1
FIG. 2
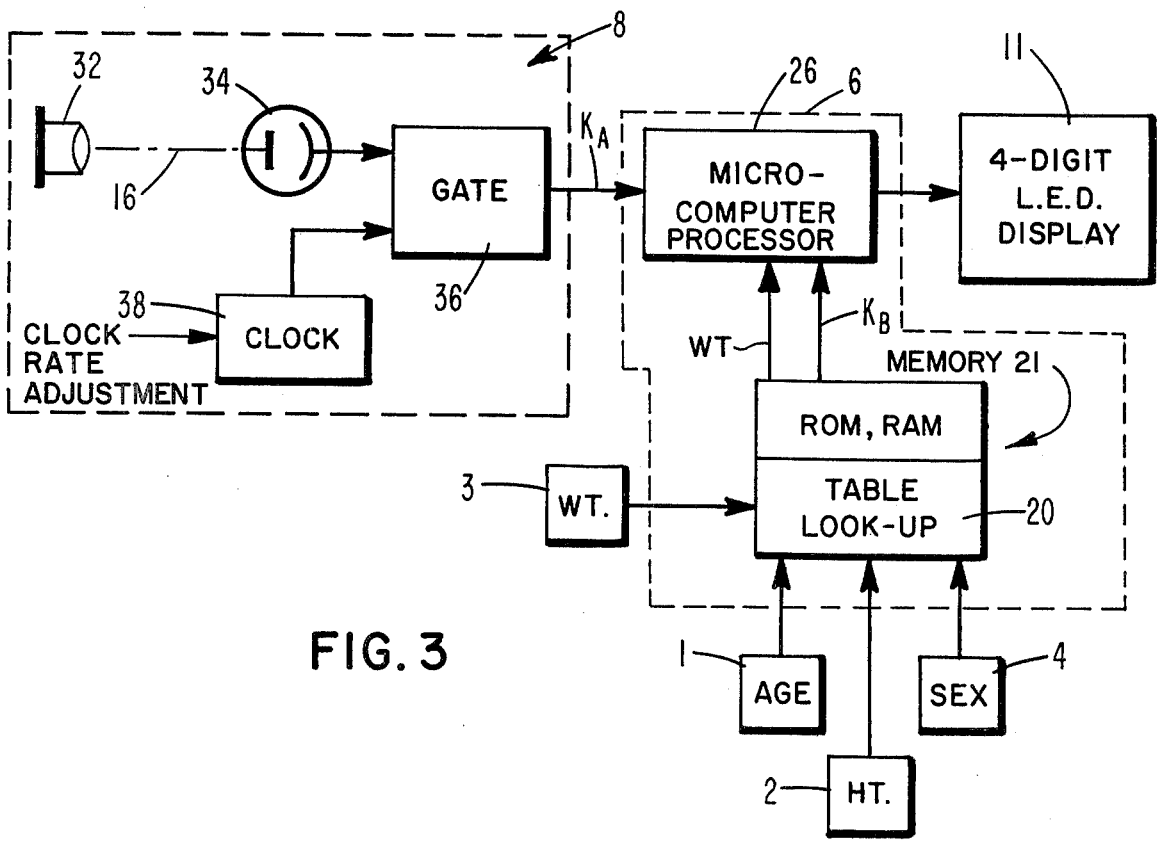
FIG. 3

ELECTRONIC CALORIE COUNTER

FIELD OF THE INVENTION

This invention relates to an exercise meter, and more particularly to an exercise measuring system wherein the total calories consumed by the exerciser is measured utilizing equations which take into account the physical parameters of the exerciser, and the quantity is visibly displayed.

BACKGROUND OF THE INVENTION

Exercise metering devices have a long history in the prior art. For example, Kerwin U.S. Pat. No. 3,511,097 shows a bicycle-type exercise apparatus connected to electronic circuitry including current integrators for measuring the energy output of the bicycle apparatus and giving a continuous count indication of the amount of exercise. However, most people for whom exercise is prescribed or desired wish to have greater freedom in their choice of the exercise to be performed than is provided with such a stationary system. A similar device showing calories expended on an electronic readout also is disclosed in Barron U.S. Pat. No. 3,984,666. However, this system suffers from the same limitation as the Kerwin apparatus.

In an attempt to break away from the limitations of these prior art devices, it has been proposed to provide a magnetic accelerometer, such as shown in Tognola U.S. Pat. No. 3,129,347 which has a magnet as a moving part therein, to detect the amount of motion by the user. It has been further proposed to provide the housing of this accelerometer, shown for example in FIG. 1, with a mechanical switch such as a reed switch to determine when the movable magnet moves within proximity of the stationary magnet because of the force of the motion of the user. While this device is of interest as a basic concept, it is not a commercially practical system because the mechanical system for measuring magnet positioning is subject to inaccuracy caused by magnetic field variations and breakdown problems inherent in such mechanical structures.

It has also been proposed as an alternative means for detecting activity that a magnet be placed adjacent a pickup coil as shown in Bornmann U.S. Pat. No. 3,547,106. Such a position-detection pickup coil (which is also shown in the Tognola patent) is expensive to implement; its output signal requires substantial circuitry for processing, as shown in block form in FIG. 1 of the Bornmann patent, which includes a band pass filter, rectifier, trigger, multivibrator, timer and flip-flop.

Obviously, simplified position-detecting circuitry for the transducer to provide an accurate, reliable signal was necessary to provide a commercially feasible device. Further, the piror art devices did not include means for establishing the physical condition of the user as a variable in measuring calorie consumption.

SUMMARY OF THE INVENTION

The subject invention provides a calculator for accurately measuring calorie consumption over a period of time. The vertical component of the user's motion is measured by a motion-detecting transducer in combination with means for opto-electrically defining the position of the transducer, and translating that motion into electronic impulses per unit of time. These impulses, which are proportional to the acceleration imparted to the motion detecting transducer by movement of the user, provide one input to a processor which operates under control of a read-only memory programmed in accordance with a set of equations which take into account the physical condition of the user. The resulting output of the microprocessor provides a continuous indication of the caloric consumption by the user.

The system is enabled by the uniquely simplified means for opto-electrically defining the position of the movable magnet in the transducer comprising a light-emitting diode on one side of the transducer housing and a photo-detector on the opposite side; the output of the photo-detector is coupled to a clock-controlled AND gate. When the light from the light-emitting diode does not fall on the photo-detector, a pulse stream at the clock rate is output from the gate, and is detected and stored by the processor. The accuracy of the calculation of rate and total caloric consumption by the user is a function of the clock rate to the other input of the AND gate.

In a further improvement, a set of manual switches is provided to establish the physical condition of the user; the processor checks the state of these switches and by reference to a lookup table in memory locates a constant which represents the user's physical condition.

The calculator is controlled by a program stored in a read-only memory based on a set of equations published by V. Antonetti in "The Equations Governing Weight Change in Human Beings," *The American Journal of Chemical Nutrition*, Vol. 26, No. 1, January 1973, incorporated herein by reference. These equations allow for a very accurate calculation of a user's caloric consumption, keyed to that user's physical condition.

The basic equation relied on is
C (caloric consumption)=$E'_A + E'_A$
$E'_A$=activity function
$E'_A$=basal metabolic energy function
$C = (1/1 - \alpha)(K_a W + K_B W^n)$
$1/1 - \alpha = 1.11$
$K_a$=activity coefficient as defined by Table 1
W=weight
$K_B$=basal metabolic coefficient as defined by Table 2
n=0.425 α is an allowance for the specific dynamic action of food.

Table 1

| Values of activity coefficient $(K_A)^n$ | |
|---|---|
| Level of activity | $K_A$(kcal/lb/day) |
| Sedentary | 3.68 |
| Light | 4.32 |
| Moderate | 5.75 |
| Vigorous | 8.00 |
| Severe | 12.30 |

Table 2

Values of basal metabolic coefficient $(K_B)^a$
Surface area method: $K_B = E'_B/W^{0.425} = 0.241 (B)(H)^{0.725}$

| | | Height, inches | | |
|---|---|---|---|---|
| Sex | Age | 60 to 66 | 66 to 72 | 72 to 78 |
| Male | 18–35 | 186 | 199 | 210 |
| | 35–55 | 175.7 | 183.5 | 199 |
| | 55–75 | 164 | 171.5 | 186 |
| Female | 18–35 | 180 | 182 | 192 |
| | 35–55 | 164 | 171.5 | 186 |
| | 55–75 | 154.5 | 162 | 175 |

BRIEF DESCRIPTION OF THE DRAWINGS

FIG. 1 is a block diagram of the electronic calorie counter described in this application.

FIG. 2 illustrates the magnetic motion sensor shown in block form in FIG. 1.

FIG. 3 shows in greater detail portions of the system shown in FIG. 1.

DETAILED DESCRIPTION OF THE INVENTION

The electronic calorie counter disclosed herein is especially designed for use in defining the amount of calories consumed by a user over a known period of time. The calculator operates by sensing the motion of the patient and translating the vertical component of that motion into electronic impulses. By using an electro-optic position sensor in combination with a magnetic motion transducer, a clock time signal is developed wherein the number of impulses over a period of time is proportional to the acceleration sensed; calories consumed may therefore be calculated as a function of the number of impulses sensed.

The energy utilized by an individual is also a function of the morphology and age of the individual using the calculator. The instant invention includes means for establishing these constants by dialing into the calculator the height, weight, age, and sex of the individual user. This is accomplished using a set of selector switches, 1, 2, 3, 4 shown in FIG. 1. These switches provide constants which are required by the microcomputer 6 in calculating calories consumed.

In addition to these constants, the program equations stored in read-only memory of the micro-computer 6 (see FIG. 3: a portion of memoryy 21) require the output of energy sensor 8 for the micro-computer 6 to calculate and display on display 11 the calories consumed. The motion sensor 8 itself comprises, as shown in FIG. 2, a housing 10 having a first fixed magnet 12 and a second magnet 14 which is slidable in the housing 10. It can be seen that the magnets 12, 14 are aligned with like poles facing each other so that in the equilibrium state, the magnets 12, 14 are spaced apart. An electric-optic axis 16 is defined by means as shown in FIG. 3 for detecting movement of the floating magnet 14; movement of this magnet is a mechanical analog of the vertical component of motion of the user. The motion detecting magnetic transducer 8 operates in accordance with the principles described in the Tognola patent. The transducer is incorporated in a structure such as a fountain pen type clip so that the wearer will normally carry it on his person with the axis of the transducer aligned with the motion which is to be sensed, that is the vertical component of body motion.

As shown in FIG. 3, the micro-computer 6 comprises processor section 26 and memory 21 which includes table look-up portion 20 and a ROM portion and a RAM portion. The sex, height, weight and age are dialed in on switches 1, 2, 3 and 4; micro-computer 6 reads these switches and addresses a table lookup portion 20 of the memory 21 to provide a constant $K_B$ to the processor 26. The person's weight is also directly supplied as an input to the microcomputer 6 and stored by memory 21 for subsequent calculations by the processor. The third essential input needed to provide the information necessary for calculating the rate of energy consumption is provided by position detecting logic (FIG. 3) associated with sensor 8.

To form this third input, the user's motion is translated into a time-based signal by sensing the position of the movable magnet 14 relative to the electro-optic axis 16. This axis 16 is defined using a light-emitting diode 32 and photo-electric detector 34. When the movable magnet 14 is displaced downwardly toward the fixed magnet 12 across the electric-optic axis 16, the light output of the light-emitting diode 32 to the photo detector 34 is interrupted. While the light is interrupted, the gate 36 passes the clock signals from clock generator 38 to the processor 26 which counts and stores the pulses received during a given period of time. The force of repulsion between the like poles of magnets 12 and 14 eventually forces the movable magnet 14 back across the electric-optic axis and towards its equilibrium position, ending the pulse stream. The number of pulses accumulated over a period of time defines the constant $K_A$. The number of pulses accumulated over a time period will vary with the severity of the exercise undertaken, as the movable magnet 14 will cross the axis more frequently with increased exertion. The output $C_T$ (calories consumed over a period of time) is calculated by processor 26 as a function of the weight, $K_A$ and $K_B$ in accordance with the equations shown in the Antonetti article.

As shown in FIG. 3, the calories consumed are displayed in the form of a four-digit light-emitting diode display 11 whose least significant bit is in units of 10 calories. Normal activity should generate between 2,000 and 4,000 calories per day, so the calculator can accumulate up to one month of calorie consumption. However, the display is illuminated only when a switch on the device is depressed. This preserves the battery which is contained within the unit. Such a switch may be, for example, incorporated in the cap of the pen-like design which is the preferred embodiment of this invention. Depressing the switch twice in rapid succession zeros the device.

In use, the device is worn on a person's body, carried in a shirt pocket or attached to a belt. The individual's characteristics are established for the calculator by aligning four rotary switches 1, 2, 3, 4 on the lower half of the pen to correspond to the individual's height, weight, age and sex. Thereafter operation is completely automatic.

Because an individual user will expend energy even in a sedentary mode, the calculator will continue to accumulate a basic number of calories consumed even though no exercise is being carried on and therefore the electro-optic axis is uncrossed 16 by the transducer's magnet 10. Consequently, the calculator provides a complete measure of calories consumed for any length of time the user wishes.

I claim:

1. An electronic consumption calculator including
(1) an activity sensor having
  (a) a housing, a first magnet having a fixed position in said housing
  (b) a second magnet movable within said housing and having a pole aligned to confront the same pole on said fixed magnet so that the second magnet occupies a reference position at a distance from said first magnet, and
  (c) a means for defining an axis between said first magnet's fixed position and said second magnet's reference position, said axis being intercepted by said second movable magnet in response to activity by a user of said calculator, and (2) means for calculating the number of calories expended in the course of said activity comprising
   (a) means for defining a first variable as a function of the time the second magnet intercepts said axis,
   (b) means for deriving a second variable as a function of the physical characteristics of said user including age, sex, height and weight, and
   (c) processing means for calculating and displaying the number of calories expended on the basis of said first and second variable.

2. A calculator as claimed in claim 1 wherein said means for defining said time variable comprises a clock controlled gate having first and second input terminals, said first input terminal coupled to said means for defining an axis, the time duration of interception of said axis by said second magnet being defined by the output of said clock gate.

3. A calculator as claimed in claim 2 wherein said means for deriving said second variable comprises
   a memory having a table look-up portion, and
   a plurality of manual switches for defining the physical characteristics of said user,
   said processing means scanning said manual switches and, responsive thereto, deriving said second variable from said table look-up portion.

4. A calculator as claimed in claim 3 wherein said means for defining an axis comprises a light-emitting diode on one side of said housing and a photo detector on the opposite side of said housing.

5. A calculator as claimed in claim 2 including a clock pulse source connected to the second input terminal of said clock gate and including means for calibrating the number of impulses per unit time to correspond to a specific force applied to the upper magnet to allow for variations of the magnets in production.

* * * * *